(12) United States Patent
Stenberg et al.

(10) Patent No.: US 7,108,652 B2
(45) Date of Patent: Sep. 19, 2006

(54) MULTI-CHAMBER SELF-REGULATING VENTRICULAR ASSIST DEVICE

(75) Inventors: Mattias G. Stenberg, Gainesville, FL (US); Roger Tran-Son-Tay, Gainesville, FL (US); Charles T. Klodell, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 56 days.

(21) Appl. No.: 10/862,659

(22) Filed: Jun. 7, 2004

(65) Prior Publication Data
US 2005/0288543 A1    Dec. 29, 2005

(51) Int. Cl.
*A61M 1/12* (2006.01)
(52) U.S. Cl. ....................................................... 600/16
(58) Field of Classification Search ................... 600/16
See application file for complete search history.

(56) References Cited

U.S. PATENT DOCUMENTS

| | | | |
|---|---|---|---|
| 3,911,897 A | 10/1975 | Leachman, Jr. | |
| 4,645,877 A | 2/1987 | Curtin | |
| 4,648,877 A | 3/1987 | Lundback | |
| 5,147,281 A | 9/1992 | Thornton et al. | |
| 6,264,601 B1 * | 7/2001 | Jassawalla et al. | ............ 600/16 |
| 6,443,884 B1 | 9/2002 | Miyawaki | |

FOREIGN PATENT DOCUMENTS

| | | |
|---|---|---|
| EP | 0074733 | 3/1983 |
| EP | 1191956 | 4/2002 |

* cited by examiner

*Primary Examiner*—Scott M. Getzow
(74) *Attorney, Agent, or Firm*—Akerman Senterfitt; Neil R. Jetter

(57) ABSTRACT

A multi-chamber ventricular assist device (VAD) for blood pumping includes a rigid outer housing having an inlet and outlet, a pre-filling chamber disposed within the housing fluidly connected to the inlet, and an a ejection chamber disposed within the outer housing. A movable plate is flexibly secured to the housing and is in a flow path of the blood being disposed between the pre-filling and the ejection chamber. The movable plate has a one-way valve for flowing blood from said pre-filling chamber to the ejection chamber. An outlet valve is disposed between the ejection chamber and the outlet of the device. A structure is provided for moving the movable plate. The multi-chamber VAD is suitable as a heart prosthesis which can be implanted in the body or used externally.

20 Claims, 8 Drawing Sheets

MULTI-CHAMBER SELF-REGULATING VENTRICULAR ASSIST DEVICE

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention is a multi-chamber self-regulating ventricular assist device (VAD) which is suitable as a heart prosthesis which can be implanted in the body.

BACKGROUND OF THE INVENTION

According to the National Heart, Lung and Blood Institute, an estimated 4.8 M Americans have congestive heart failure (CHF), a condition in which the heart cannot pump enough blood to meet the need of the other organs of the body. The heart grows too large as a result of congestion in the tissues which also effect the lungs and extremities such as the legs. CHF is a chronic condition and is often the end-stage of cardiac disease. Half of all patients diagnosed with CHF are generally dead within 5 years. The disease is present in about 10% of all persons over 70 years of age and each year there are an estimated 400,000 new cases in the U.S. alone.

Treatment options are limited. Drugs, such as diuretics, ACE inhibitors and digitalis are primary therapy and are used to either expand blood vessels or eliminate access salt and water in the body. For late stage patients, heart transplants are an option but the supply of donor hearts are very limited. American Heart Association (AHA) data puts cost of care for CHF patients at $20B annually in the U.S. Actual dollars could be as high as $30–35B given the overlap with other cardiovascular disease states. Various anecdotal data suggests that the per capita spending in Europe is even higher. Thus, CHF is a highly prevalent, chronic disease, with limited treatment options and a very high cost of care on a global basis.

Addressing the importance of alternative therapies to heart transplants for CHF patients, the clinical unmet need is ever increasing, and rapidly. For patients with late-stage CHF current treatment options are limited. Excluding the use of cardiac assist technologies such as VAD-based systems, the only viable treatment option available today is a heart transplant. In recent years, the number of available donors has stabilized at 2,300 per year. However, with the benefits of better health care, more CHF patients are reaching late-stage status, further increasing the need for transplants. As a result, the gap between the number of available donors and the number of patients on the transplant list have doubled in the last 10 years, reaching close to 5,000 patients in the US alone. But even this figure misrepresents the actual need for late-stage treatment, as the screening criteria for acceptance to the transplant waiting list are immediately disqualifying roughly 50 percent of all patients. Calculations by the American Heart Association show that the actual number of US patients in need of late-stage treatment is about 40,000, only counting those 65 years old or younger.

Ventricular Assist Devices are used to off-load the heart and take over the heart's pumping functions. VAD designs originate from other industrial pump applications. The first generation of VADs comprised ordinary displacement pumps. Since then many techniques have been applied in the design of new VAD systems, such as centrifugal pumps and impeller (turbine) pumps.

VADs are currently used for both acute and chronic cases of heart failure. VADs ensure that the vital organs get sufficient blood flow and allow more time to find a suitable heart donor (bridge-to-transplant), as well as time to build strength and improve the patient's general condition before a transplant. Due to the relatively good portability of many current VAD systems, many patients may be able to return to their homes and even to their jobs while awaiting transplantation. This may drastically improve quality of life and reduce the cost associated with extended hospital stays. Most of the VAD systems currently available are used as bridge-to-transplant systems.

It has also been found that VADs can improve the condition of the diseased heart itself. By off-loading the heart for an extended period the heart can rest and sometimes heal itself. This is often referred to as bridge-to-recovery VADs. The use of VADs for this purpose includes not only CHF patients, but also patient categories such as viral myocarditis patients and cardiogenic shock patients. Cardiogenic shock is currently seen in approximately 4 percent of all post cardiotomy patients. Even though some of the VAD systems available today may be used as bridge-to-recovery VADs, they are all generally designed as bridge-to-transplant systems.

Additionally, many CHF patients are elderly and for other reasons might not qualify for a heart transplant. There are also other CHF patient categories where a heart transplant is deemed in vane. For that purpose, VADs or Total Artificial Hearts (TAHs) might be able to provide a viable alternative. Due to the recent FDA approval of the HeartMate VAD system as a destination therapy for patients not eligible for heart transplants, this is likely to drastically increase the market for VAD systems.

Despite the many advances in VAD technology, current devices generally have the several common shortcomings. VAD devices may be too large for transplantation into patients with smaller frames. This excludes many women and children. Many of today's VAD systems require advanced computerized control systems to regulate the function of the pump. Such VADs are costly and labor intensive to operate, excluding many under developed markets. This may also have prevented VAD systems from finding widespread acceptance and use for extended fields of applications in non-surgical settings, such as cardiogenic shock in the ER, ICU, or PTCA laboratory.

SUMMARY

A multi-chamber ventricular assist device (VAD) for blood pumping includes a rigid outer housing having an inlet and outlet, a pre-filling chamber disposed within the housing fluidly connected to the inlet, and an a ejection chamber disposed within the outer housing. The outer housing is preferably hermetically sealed.

A movable plate is flexibly secured to the housing and is disposed between the pre-filling and the ejection chamber. The movable plate has a one way valve for flowing blood from the pre-filling chamber to the ejection chamber. Thus, the movable plate is in the flow path of the blood. An outlet valve is disposed between the ejection chamber and the outlet of the device. A structure is provided for moving the movable plate. The multi-chamber VAD is suitable as a heart prosthesis which can be implanted in the body, or used externally.

VADs according to the invention provide high efficiency which permits a pumping capacity required for a given application to be obtained with a device having a significantly smaller size than possible using currently available VAD designs. Small size permits pediatric VAD applications which were not possible before the invention. Another important feature of the invention is the self-regulating feature, where blood output by the VAD increases with the level of the physical activity of the patient. The invention also provides a pulsating outflow, together with a substantially constant inflow of blood.

As used herein, the phrase "substantially constant blood inflow" includes two (2) components. First, the flow is "constant" because there is no interruption to the inflow during the full pumping cycle. The VAD will always fill, regardless of where in the pumping cycle the device is. The inflow is also preferably "substantially constant" throughout the pumping cycle. Thus, the inflowing volume per unit time (rate) for the VAD during both the systolic and diastolic phase of the pump can remain within 10% of an average cycle value, preferably within 5%, and most preferably within 2% of the average value.

The pre-filling chamber is preferably a flexible chamber. The flexible chamber can be spaced apart from inner walls of the housing, wherein a gas holding chamber is formed between the flexible chamber and the housing. A pressure differential between the gas holding chamber and the ejection chamber can provide a passive driving force for automatic movement of the movable plate upward toward the pre-filling chamber. The cross sectional area of the pre-filling and the ejection chamber can remain substantially constant throughout cycling of the device.

The ejection chamber preferably includes rigid walls. The rigid walls of the ejection chamber can be provided by inner walls of said outer housing. The rigid walls can include a textured surface, where the textured surface promotes neointima formation.

A maximum volume of the pre-filling chamber is preferably substantially less than a maximum volume of the ejection chamber. In one embodiment, the maximum volume of the pre-filling chamber is in a ratio with the maximum volume of the ejection chamber of between 1.5:1 and 3:1, such as a 2:1 ratio.

A self-regulating method of pumping blood using a ventricular assist device (VAD) disposed within a cardiac patient includes the steps of receiving a variable inflow pressure, and automatically providing an output flow rate of blood based on the inflow pressure. A rate of blood flow monotonically increases with a level of physical activity performed by the patient. The inflow pressure is generally atrial pressure. The output flow can be a pulsating flow. The method can provide a continuous inflow rate of blood throughout a duration of a complete pumping cycle. The inflow can be at a substantially constant rate throughout the pumping cycle.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION

A multi-chamber ventricular assist device (VAD) for pumping blood includes a rigid outer housing having an inlet and outlet, a pre-filling chamber disposed within the housing fluidly connected to the inlet, and an ejection chamber disposed within the outer housing. A movable plate is flexibly secured to the housing and is in the flow path of the blood being disposed between the pre-filling and ejection chamber. The movable plate has a one-way valve for flowing blood from the pre-filling chamber to the ejection chamber. An outlet valve is disposed between the ejection chamber and the outlet of the device. A structure is provided for moving the movable plate.

Figure 1:
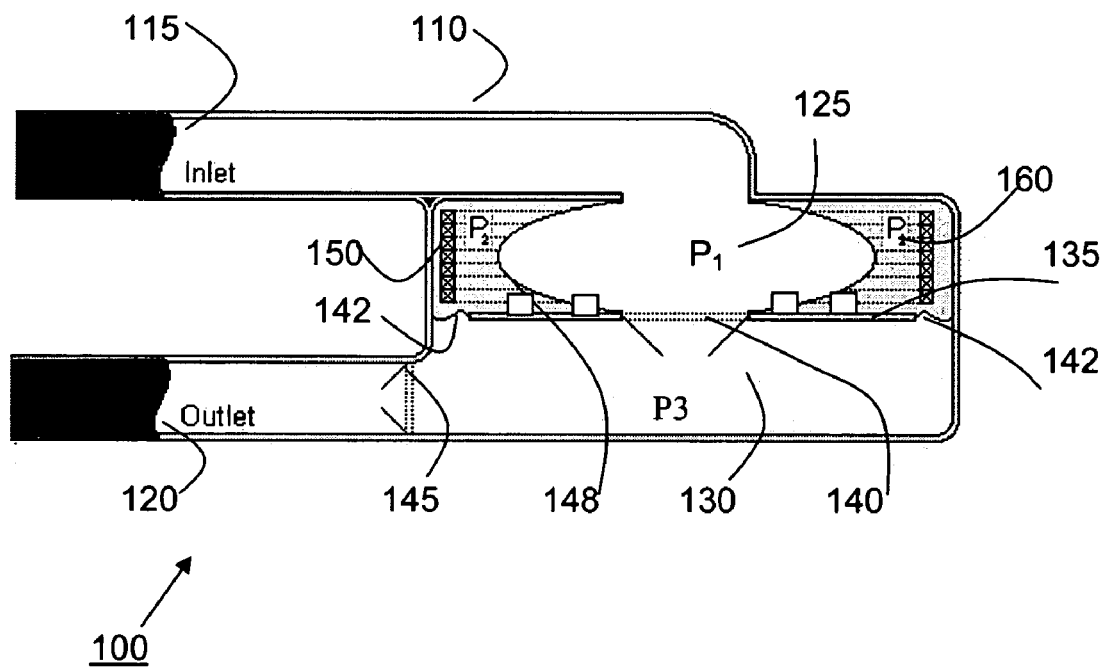
FIG. 1 is a simplified cross-sectional illustration of a multi-chamber VAD, according to the invention.

A simplified cross-sectional illustration of a multi-chamber VAD 100 according to the invention is shown in FIG. 1. VAD 100 includes a rigid outer housing 110 having an inlet 115 and an outlet 120. Rigid housing 110 is preferably formed from a metal or hard plastic. As used herein, the term "rigid" refers to a non-deformable material such as a steel, titanium or plastics whose shape does not change during normal pump operation. Such rigid materials allow for texturing and easier coating as compared to a flexible surfaces which are subject to flexing. Such rigid surfaces can be coated with drugs, which tend to remain adherent during VAD operation, such as the anticoagulant drug Heparin.

The rigid housing 110 can also be used to aid in increasing biocompatibility of VAD 100 compared to conventional blood pumps which generally use flexible surfaces. A rigid textured and coated housing surface can even enable the formation of neointima on the inside of the ejection chamber, which can advantageously simulate the inside of a native blood vessel. For example, coatings similar to the THORALON® coating which have been disclosed to promote neointima formation used in the HeartMate® VAD system produced by Thoratech Corporation (Pleasanton, Calif.) may be used with the invention. THORALON® is composed of a base polymer which provides enhanced strength, flexibility, and durability along with a surface modifying additive which promotes the neointima formation.

A pre-filling chamber 125 is disposed within the housing 110 and is fluidly connected to the inlet 115 for receiving blood. The pre-filling chamber 125 is preferably a flexible chamber, such as made from a flexible bulb shaped biocompatible membrane material. Pre-filling chamber 125 is preferably formed from a biocompatible polymer, such as polyurethane. As defined herein, the term "flexible" refers to a readily and substantially deformable material whose shape changes during pump operation, such as the substantial deformation of the pre-filling chamber 125 an associated volume change of at least 20% and generally 100% or more, as demonstrated during the cycling shown in FIGS. 4–8.

The cross sectional area of both ejection chamber 130 and pre-filling chamber 125 are held constant throughout operation of VAD 100. The cross sectional area of ejection chamber 130 is constant because it is defined by the inner walls of the rigid pump casing comprising housing 110. The diameter and thereby its cross sectional area is thus fixed throughout the pumping cycle. The pre-filling chamber 125 is made in such a way and shape that the actual diameter (and thereby cross sectional area) does not change as the pre-filling chamber 125 is compressed/extended throughout the pumping cycle.

Pre-filling chamber 125 is shown spaced apart from the inner walls of housing 110. This volume 160 is referred to herein as a gas holding chamber 160. Gas holding chamber 160 can be filled with a low-density gas (e.g. helium) or be exposed to atmospheric pressure. The gas pressure in the gas holding chamber 160 can be pre-set by the operator before use by extracting gas or pumping more gas intro the chamber 160. The inlet pressure is the pressure of the left atrium of the human heart. This is typically in the range of 2–20 mmHg. A value above 10 mmHg is typically found in congestive heart failure patients. If the pressure in the gas compartment is set at a level lower than the lowest possible inlet pressure (approx 2 mmHg), when the movable plate 135 is at its top position in the cycle and the gas holding chamber 160 is compressed to its minimum volume, the gas pressure inside can not exceed the inlet pressure during operation, as the volume of the gas holding chamber compartment 160 will increase and the gas pressure will as a result drop.

VAD 100 also includes an ejection chamber 130 which is also disposed within the outer housing 110. Ejection chamber 130 shown in FIG. 1 is a rigid chamber which utilizes the inner walls of rigid housing 110. In an alternate arrangement (not shown), housing 110 can utilize one or more dedicated rigid portions, thus not utilizing inner portions of housing 110. A movable plate 135 is flexibly secured to the housing 110 and is disposed between the pre-filling chamber 125 and ejection chamber 130. The flexible connector 142 maintains adhesion to a fixed portions of the inner walls of housing 110 as movable plate 135 moves up and down during cycling of VAD 100. Flexible connector 142 can be formed from biocompatible membrane-like materials including polyurethane. The flexible connector 142 can be secured to movable plate 135 using a variety of arrangements. In one arrangement, flexible connector 142 is glued or bound using another adhesive to movable plate 135 and further secured to the movable plate 135 by one-way valve 140. The flexible connector 142 can be connected to the outer housing 110 by pressing it between the upper and lower portions of the housing 110. The upper and lower portions of housing 110 can be secured together externally.

The movable plate 135 has a one way valve 140, such as a mitral valve, located near its center for flowing blood from the pre-filling chamber 125 to the ejection chamber 130. Thus, movable plate 135 of VAD 100 is clearly within the flow path of the blood. In contrast, in conventional VADs the movable plate is remotely located relative to the flow path of blood. The inventive arrangement enables the movable plate 135 to compress one chamber (125 or 130) at the same time as it extends the other. In contrast, conventional displacement type VAD's have only one chamber. The sole chamber in such systems is compressed by a moving platform which is commonly referred to as a "push plate". As there is only one chamber to compress to achieve ejection of blood from such conventional VADs, the platform is mounted in a 90 degree angle to the blood chamber and thus the blood flow.

Movable plate 135 is shown in its maximum upward position in FIG. 1. In this arrangement, the ejection chamber 130 is at its maximum volume while the volume of pre-filling chamber 125 is at its minimum. As noted below, compared to when the volume of ejection chamber 130 is at its maximum, the maximum volume of pre-filling chamber 125 is substantially less than a maximum volume of the ejection chamber 130, such as in a ratio of at least 1.5:1, such as about 2:1. When the ratio of the maximum volume of the ejection chamber 130 and the pre-filling chamber 125 is 2:1, VAD 100 will fill by 50% during the ejection phase (when the platform is pushed down) and by the remaining 50% during the motion of the movable plate 135 to its upper position (diastolic phase). If the two phases that make up one pumping cycle are equal in time, the inflow will be constant with this 2:1 volume ratio. However, if VAD 100 is operated in a way that the ejection phase takes 30% of the total time it takes to complete one cycle (and the diastolic phase 70%), the volume is preferably adjusted so that 30% filling is achieved during the ejection phase and 70% during diastole.

One unique feature of movable plate 135 is that it generally returns to its uppermost position on its own, without the need for any active force being applied. This is due to the pressure gradient which is created during operation of VAD 100 that acts on movable plate 135. This inventive aspect is described in detail below. To help describe pressure dynamics of VAD 100, in FIG. 1, as well as FIGS. 4–8, P1 represents the pressure in the pre-filling chamber 125, P2 represents the pressure in gas holding chamber 160, and P3 represents the pressure in the ejection chamber 130.

An outlet valve 145 which functions as an aortic valve is disposed between the ejection chamber 130 and the outlet 120 of VAD 100. Outlet valve 145 opens to flow blood from ejection chamber to outlet 120 when a predetermined pressure is built up in ejection chamber 130.

A structure is provided for moving the movable plate 135. As shown in FIG. 1, the structure for moving the movable plate 135 comprises a magnetic actuation arrangement. The arrangement shown in FIG. 1 includes a magnetic field source 150 together with movable plate 135 which includes magnets 148 mounted thereon. In an alternate related arrangement (not shown), movable plate 135 can include magnetic material therein.

Magnetic field source 150 in FIG. 1 is shown as a coil 150 disposed in gas holding chamber 160. Although not shown, alternative coil placements include one coil on top of the pump housing and one below (with this dual coil arrangement the inlet and outlet, respectively, would pass through the coils, and one coil mounted outside the vertical part of the pump outer housing (extending from the top to the bottom). Alternatively, as noted above, the magnetic actuation arrangement can rely on a fixed magnet or a plurality of such magnets. Coil 150 provides a current controlled electromagnet. The power to drive the coil 150 can be provided by an internal or external battery. Internal batteries can be recharged using non-invasive energy transfer coil systems known in the art. Coil 150 produces a magnetic field oriented substantially perpendicular to the plane of movable plate 135 when movable plate 135 is in its maximum upward position as shown in FIG. 1.

The magnets 148 on movable plate 135 are repelled as the magnetic field is activated by flowing current though coil 150, thus pushing movable plate 135 downward. The field is deactivated as the movable-plate 135 reaches its end position and then movable plate 135 passively moves back up to begin another cycle. In a preferred embodiment the power to coil 150 is turned of, deactivating the magnetic field, when the movable plate 150 has reached the lowermost (end) position. Alternatively, the polarity of the field can be reversed, such as by reversing the direction of current flowing in coil 150, resulting in a net force pulling the movable plate 135. This method can be used if the internal pressure gradient acting on the platform is not enough to relocate the platform back up fast enough, such as for high frequency operation of generally >100 beats per minute.

Plate position can be monitored in several ways. However, since end position is generally only of interest as noted above, a simple internal switch that gets triggered as the movable platform comes to its end position can be used.

Other actuating systems may be used with device 100. For example, push rods actuated by a linear motor can be used for actuation. The push rods can be connected to a linear motor or to an air cylinder powered by pneumatic power. If a linear motor is used the push rods can be operated simply by continuous operation of the linear motor. The push rods can also be fixed to the movable plate 135 creating a pull back effect on the platform (if needed in high frequency operation). If a pneumatic powering mechanism is used, a drive pressure is applied to the air cylinder, which will displace the push rods and the movable platform. The rods can be retracted by applying a vacuum to the cylinder.

Figure 2:
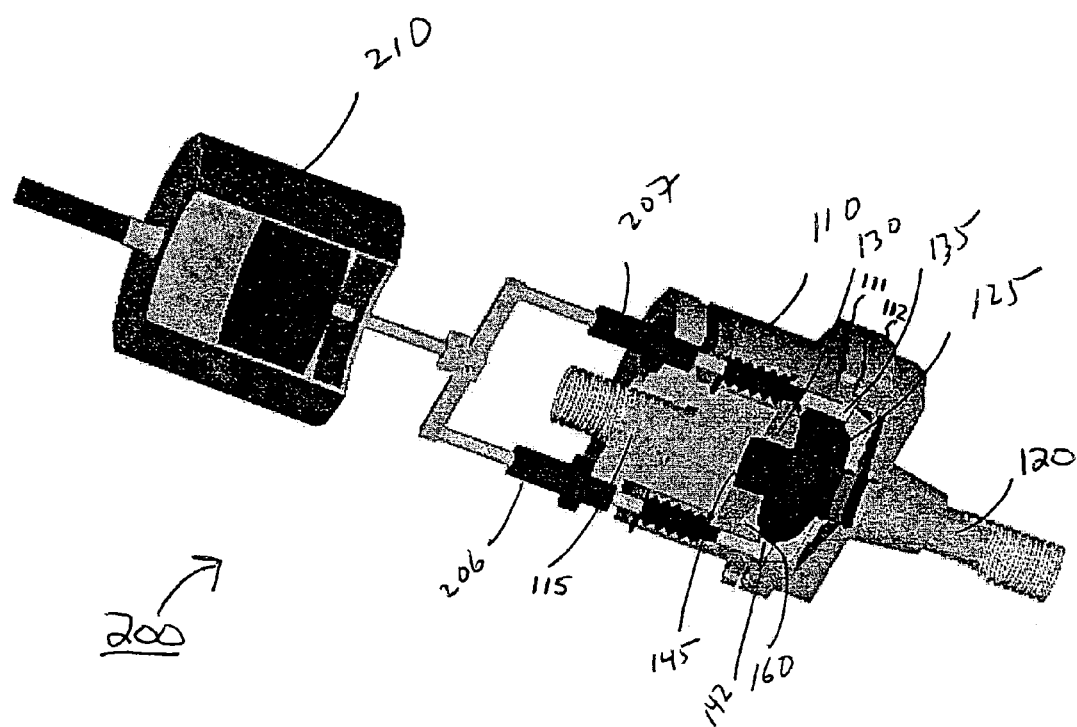
FIG. 2 shows a cut-away view of exemplary push rod actuated VAD used for initial in-vivo testing, according to another embodiment of the invention.

FIG. 2 shows a cut-away view of exemplary push rod actuated VAD 200. The architecture and operation of VAD 200 is not different from VAD 100 other than aspects relating to the actuator. VAD 200 includes push rod actuators 206 and 207 and a pneumatically powered air chamber 160 driven by linear motor 210. VAD 200 was designed for bench testing purposes and is expected to be used for an in-vitro testing program. Features common with VAD 100 are shown having like numbers. VAD 200 reveals upper portion of housing 111 and lower housing portion 112 which as described above when pressed together can secure movable plate 135 via flexible connector 142.

Figure 3:
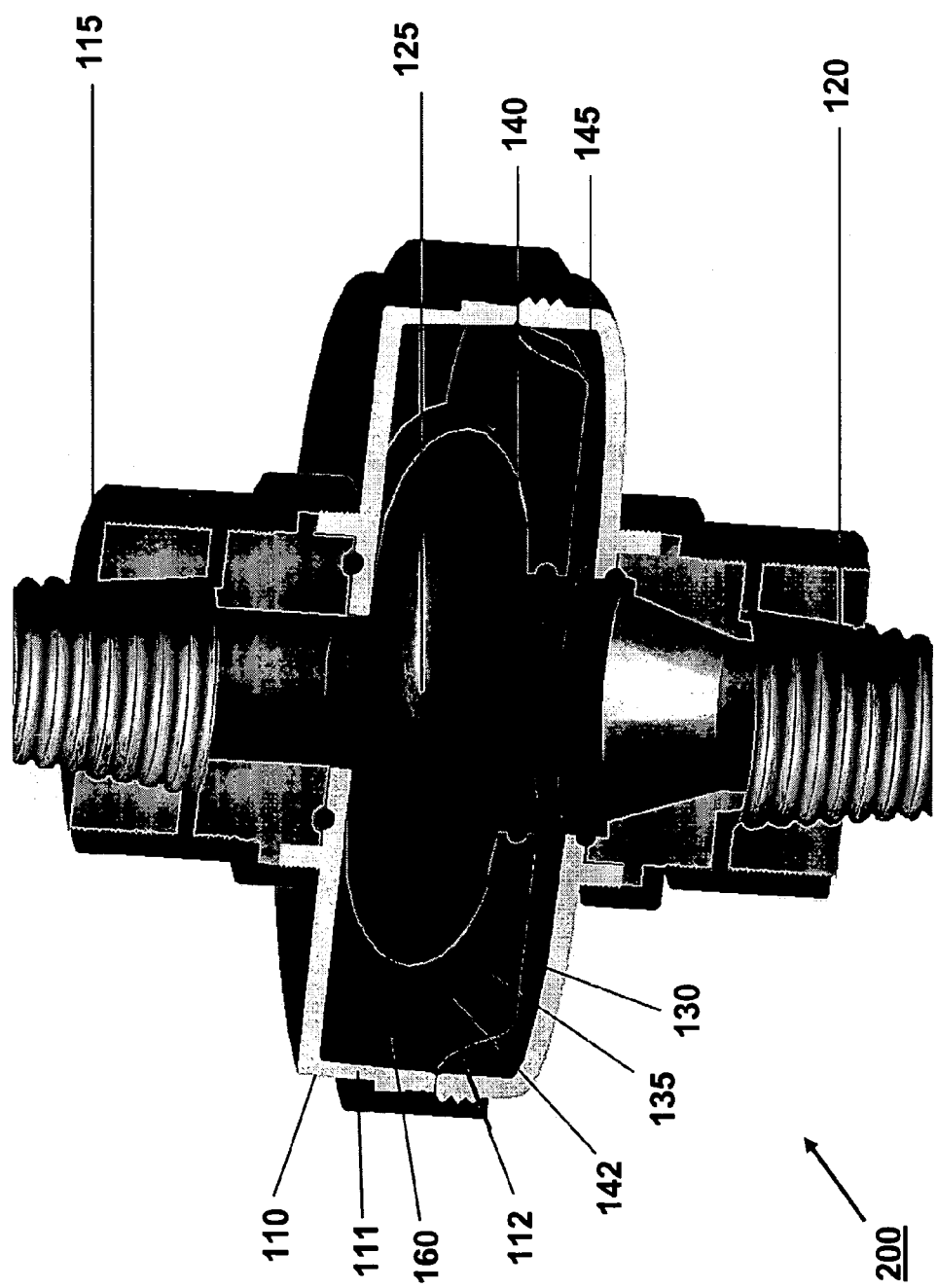
FIG. 3 is a close up view of the VAD shown in FIG. 2 where the actuator components have been omitted to more clearly reveal internal pump features.

FIG. 3 is a close up view of the VAD 200 shown in FIG. 2. The push rod actuator related components have been omitted to more clearly reveal internal pump features. For example, one way valve 140 and flexible connector 142 are more clearly shown in FIG. 3, along with their relation to movable plate 135 and housing 110 comprising upper housing portion 111 and lower housing portion 112.

A complete pumping cycle for VAD 100 or VAD 200 will now be described with the aid of FIGS. 4–8. These FIGS. each include a schematic cross section of the VAD showing valve and internal force dynamics together with a graph showing the volume of pre-filling chamber 125, the volume of ejection chamber 130, and the volume of the active filling chamber at various points in a complete exemplary pumping cycle, and specifically wherein in the cycle the particular cross sectional view shown corresponds to. The specific volumes amounts shown are provided for reference only.

Figure 4:
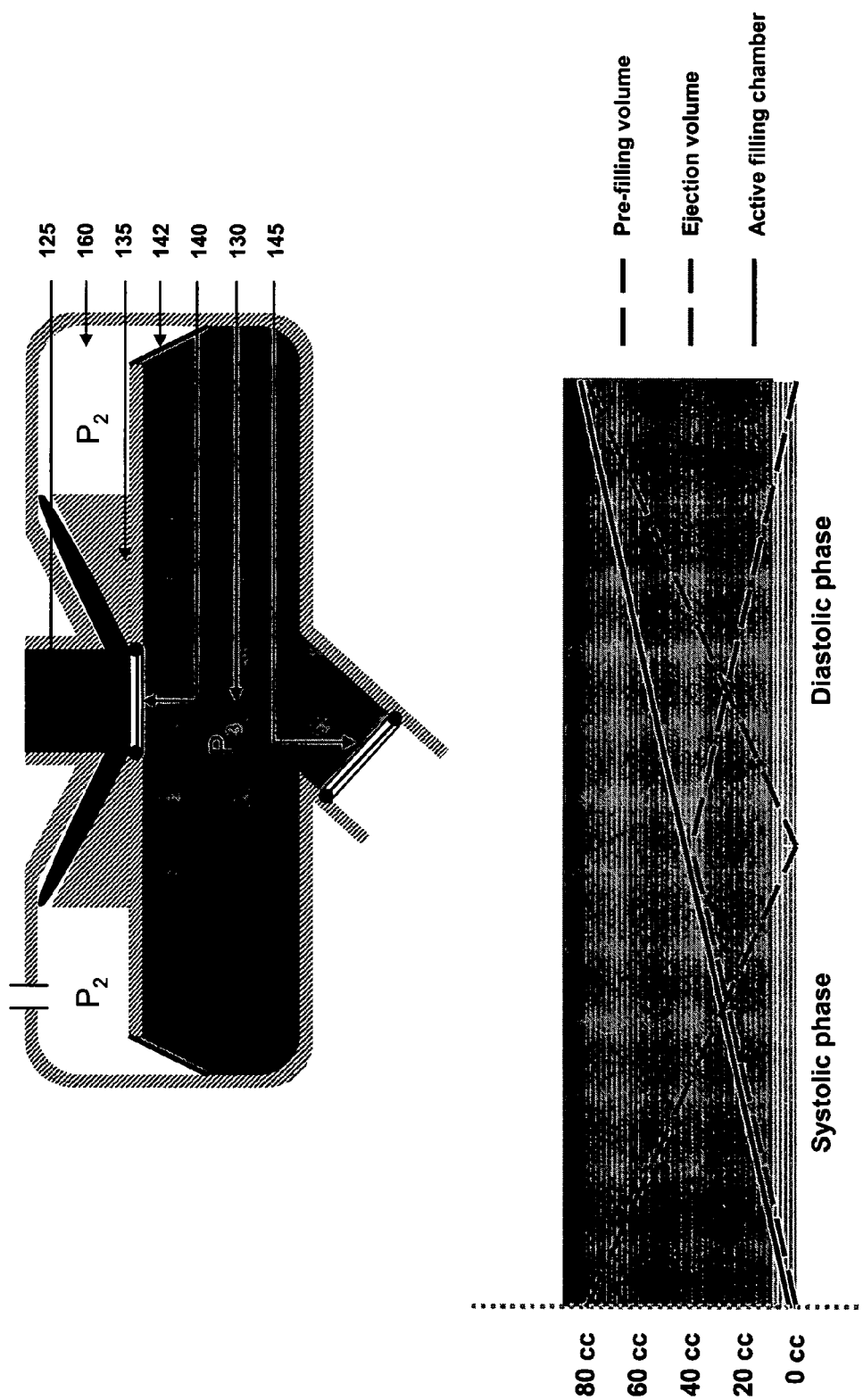
FIG. 4 shows a schematic cross section of a VAD according to the invention showing valve and internal force dynamics when the movable plate is pushed up to its maximum level.

FIG. 4 shows a schematic cross section of a VAD according to the invention showing valve and internal force dynamics when the movable plate 135 is pushed up to its uppermost level. The vent in the pictures is provided to enable the VAD to be operated with atmospheric pressure (constant pressure) inside the gas holding chamber 160. Alternatively, gas can be applied / withdrawn from the gas holding chamber 160 through this access vent by the operator. The access vent can then be sealed before operation. This represents the beginning of the pumping cycle, just before initiation of the systolic phase where blood flows out of ejection chamber 130 via valve 145. At this point in the cycle, valves 140 and 145 are both generally closed, volume of the ejection chamber 130 is at its maximum, and the volume of pre-filling chamber 125 is nearly-zero or at zero. The pre-filling chamber 125 is nearly completely compressed in FIG. 4 and as a result has a volume which is close to zero. No force is applied to movable plate 135 at this point in the cycle.

However, the pre-filling chamber 125 need not reach a near zero volume in its compressed state as the more operationally significant parameter for VAD 100 is the relative change in volume throughout the pumping cycle, not the actual volume achieved. In other words, the volume change pre-filling chamber 125 undergoes between its volume with the movable plate 135 in the top position minus volume with the movable plate 135 in its lowermost end position as the movable plate 135 is displaced, is preferably approximately at least 50% of maximum volume of ejection chamber 130. Accordingly, the pre-filling chamber 125 need not be completely compressed as long as the volume increase represents preferably at least 50% of maximum ejection chamber volume. However, for applications where minimizing the size of VAD 100 is important, such as for pediatric applications, the volume of the pre-filling chamber 125 is as close to zero as possible when movable plate 135 is in its top position.

Figure 5:
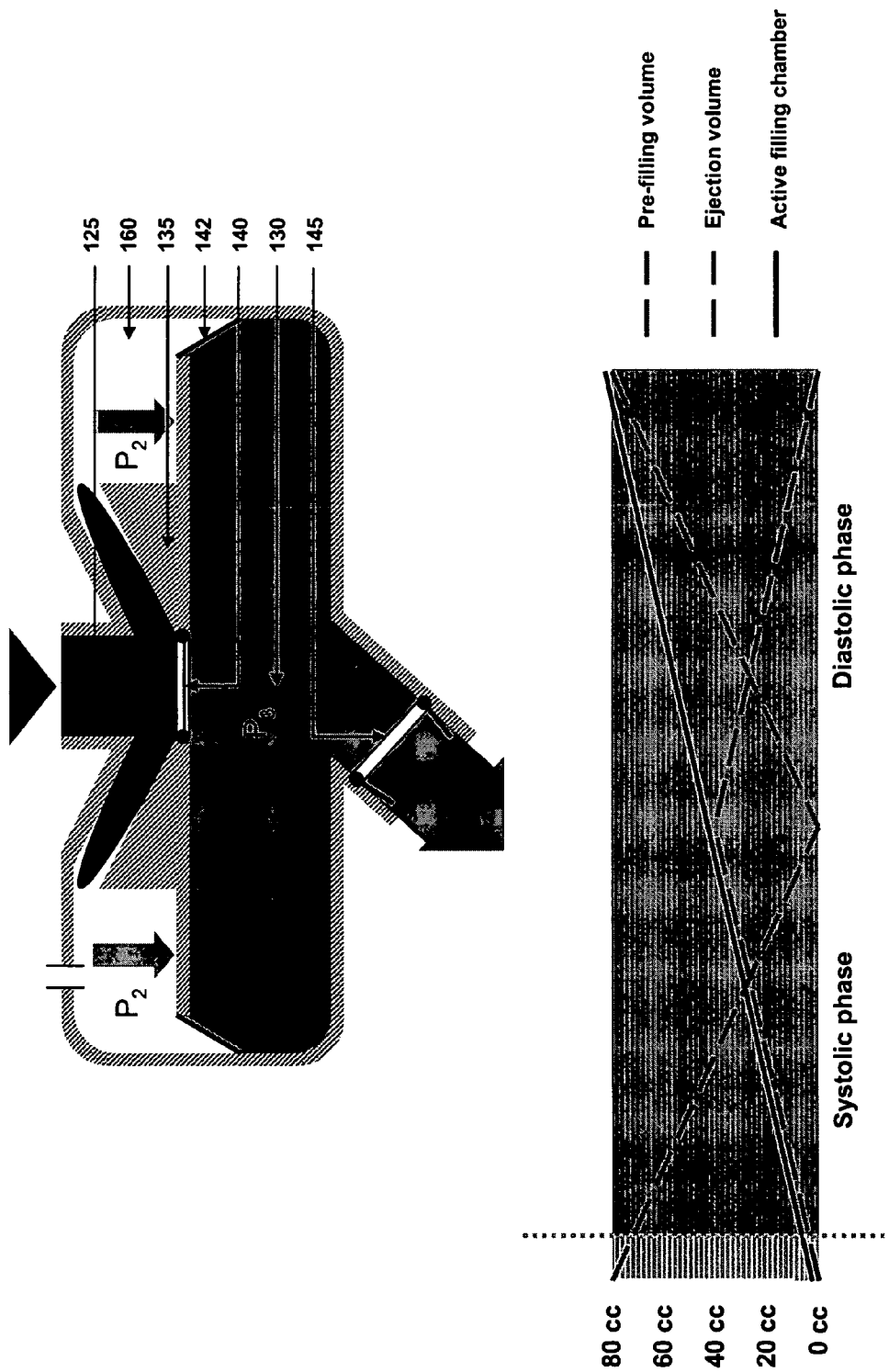
FIG. 5 shows an exemplary VAD near the begin of the systolic phase after receipt of actuation signal where the movable plate is pushed downward and the one way valve at the center of movable plate remains shut, while the outlet (aortic) valve is open.

When an actuation signal is received by movable plate 135, such as by a magnetic field produced when the coil 150 in FIG. 1 is activated by the flow of current, or by action of push rods 206 and 207 in FIG. 2, as shown in FIG. 5, the movable plate 135 is pushed downward while one way valve 140 at the center of movable plate 135 remains shut. The pressure builds up in the ejection chamber 130 as movable plate 135 proceeds downward. At some point the outlet pressure (aortic pressure) becomes exceeded, and the outlet valve 145 opens. The blood in the ejection chamber 130 is thus ejected. As the movable plate 135 is pushed down, blood is also drawn into the pre-filling chamber 125. At this point in the cycle, the volume of the ejection chamber 130 is still near its maximum, and pre-filling chamber volume is non-zero, but still near zero. When movable-plate 135 moves down during the systolic phase, the volume of chamber 160 is increased, decreasing the low-density gas pressure in gas holding chamber 160.

Figure 6:
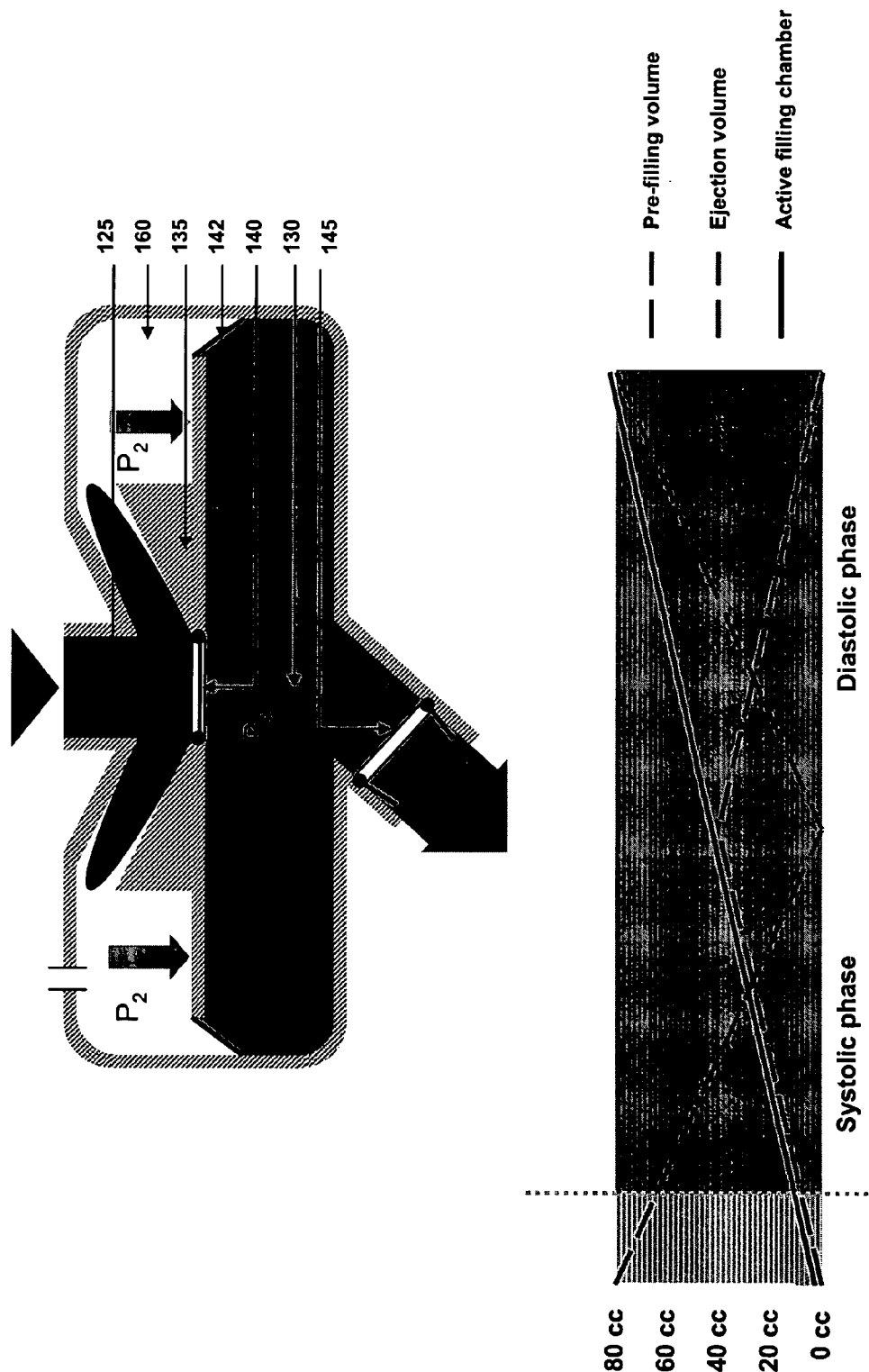
FIG. 6 shows an exemplary VAD well into systolic phase where the movable plate has moved significantly downward from its position shown in FIG. 5. The one way valve at the center of movable plate remains shut, while the outlet (aortic) valve remains open.

FIG. 6 shows the exemplary VAD well into systolic phase where the movable plate has moved significantly downward from its position shown in FIG. 5. The one-way valve 140 at the center of movable plate 135 remains shut, while the outlet (aortic) valve 145 remains open.

However, as movable plate 135 continues to be lowered, the kinetic energy of the blood remaining in the ejection chamber 130 as the movable-plate 135 reaches its end (lowermost) position will decrease due to the high resistance of the aorta which decreases the velocity of the blood in ejection chamber 130. This causes the outlet valve 145 to close as shown in FIG. 7.

When the outlet valve 145 has closed and the movable-plate 135 is at its end (lowermost) position, some blood will generally be remaining in ejection chamber 130. This blood will have a pressure just under the outlet pressure (aortic pressure). In the pre-filling chamber 125, however, the pressure is only equal to inlet pressure (e.g. left atrial pressure). This pressure gradient will also provide lift on the movable-plate 135 until the pressures in the pre-filling chamber 125 (P1) and ejection chamber 130 (P3) become the same.

Figure 7:
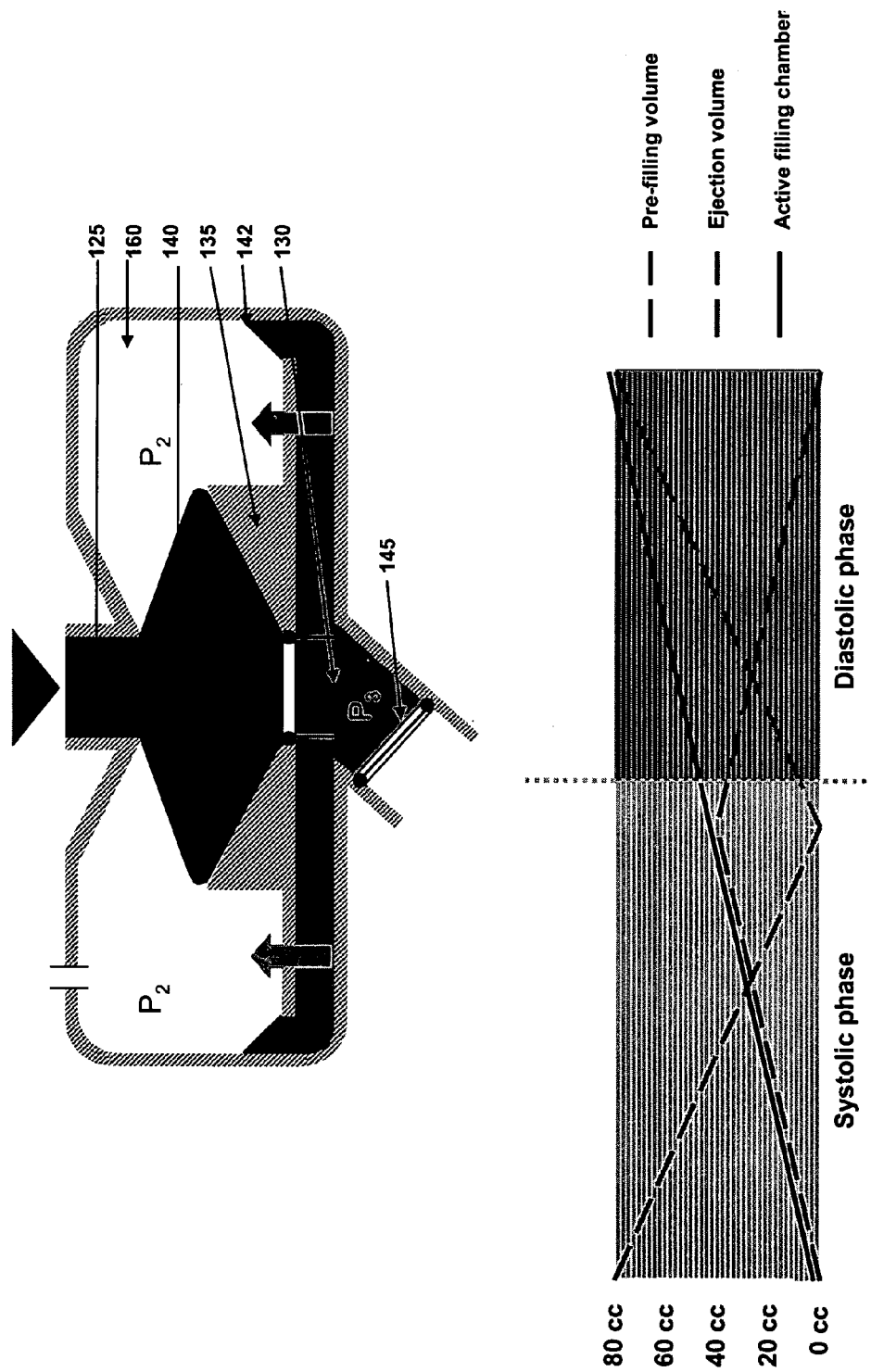
FIG. 7 shows the exemplary VAD near the beginning of the diastolic phase when a passive force begins raising the movable plate. The outlet valve is closed, while the one-way valve at the center of the movable plate is open.

The kinetic energy of the larger volume of blood in the pre-filling chamber 125 will, however, cause the one way valve 140 in movable plate 135 to open as shown in FIG. 7. Thus, blood will flow from the pre-filling chamber 125 to the ejection chamber 130, beginning the diastolic phase.

Figure 8:
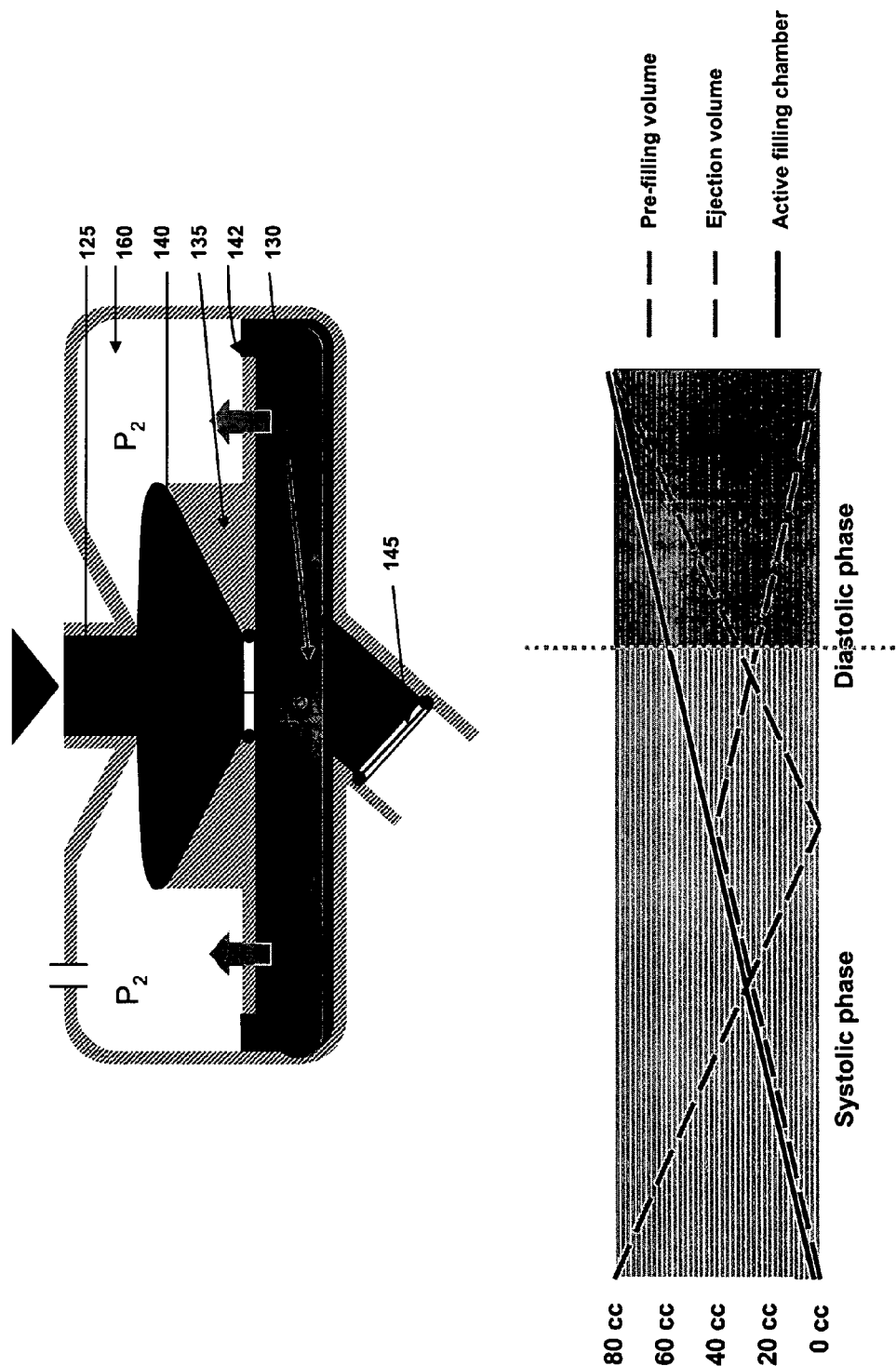
FIG. 8 shows the exemplary VAD well into the diastolic phase after the movable plate has risen significantly from its lowermost position. The outlet valve remains closed, while the one way valve at the center of the movable plate remains open.

As the cycle continues, movable-plate 135 will continue to be pushed upward while valve 140 remains open and valve 145 remains closed. Movable plate 135 will progress in its move toward its uppermost position as shown in FIG. 8. As noted above, when movable-plate 135 is moved down during the systolic phase, the volume of chamber 160 increases, decreasing the low-density gas pressure in gas holding chamber 160 even more. Since this pressure is always lower than the pressure in the pre-filling chamber 125 and the ejection chamber 130 when the one-way valve 140 is open, this pressure gradient will also provide some lift to the movable-plate 135 during its ascent. Since the pressure in the gas holding chamber 160 is designed to be lower than the pressure in the pre-filling chamber 125 and ejection chamber 130 (now acting as one chamber with a blood pressure equal to inflow pressure=left atrial pressure) the resulting pressure gradient will provide force to lift movable plate 135 back up. The pressure gradient will act on the part of the platform that extends outside of the pre-filling chamber (see FIG. 7). This will be constant throughout the pumping cycle as the cross sectional areas of the pre-filling chamber 125 and the ejection chamber 130 are constant throughout the pumping cycle.

It is noted that during the upward motion of the movable-plate 135 (diastolic phase), the one-way valve 140 is open and the pre-filling chamber 125 and ejection chamber 130 act as single active filling compartment. As the platform ascends the volume of the pre-filling chamber decreases, but the volume of the ejection chamber increases. Since the valve 140 is open and the chambers 125 and 130 act as a single chamber, the net effect is a total volume increase. This increase in volume results in blood inflow from inlet 115 to the volume defined by pre-filling chamber 125 together with ejection chamber 130.

As blood fills the ejection chamber 130 and pushes the movable-plate 135 back up, the pressure builds up in the ejection chamber 130. This causes flow to be directed to the area of lowest pressure, which is behind the leaflets (not shown) of the one-way valve 140, forcing it to close and returning the cycle to its beginning arrangement shown in FIG. 4. The inflowing blood will "jet" through the one-way valve 140. The highest pressure will be found in that jet being dynamic plus static pressure. Outside of the jet will typically have a slightly lower pressure, being principally the static pressure component. The pressure will strive to equalize in the ejection chamber 130, resulting in flow being directed to "low pressure" areas, such as behind the valve leaflets.

If one-way valve 140 is not fully closed when movable-plate 135 reaches its uppermost position, such as due to insufficient pressure in the ejection chamber 130, the one-way valve 140 will close as soon as the movable-plate 135 starts to move down again. However, regurgitation will generally not appear at the open valve 140, since the inflow is constant during the relocation of the movable-plate due to the increasing total volume of the ejection chamber 130 and pre-filling chamber 125 when the movable-plate 135 relocates. This increasing volume fills up by increased blood inflow.

In summary, lift of the movable-plate 135 is achieved in multiple different ways. The pressure gradient between the ejection chamber 130 and pre-filling chamber 125 provides lift as long as the pressure between the chambers 125 and 130 differs (when one-way valve 140 is closed). In addition, the difference in pressure between gas holding chamber 160 and ejection chamber 130 generates a pressure gradient which provides lift to the movable-plate 135. Since the time it takes for movable the movable-plate 135 to move back to its uppermost position is related to the magnitude of the pressure gradient described above, the cycle time of VAD 100 is reduced as the pressure gradient increases.

Because the time it takes for the movable plate 135 to relocate from its lowermost end position to its upper position is dependent only on the force acting on the plate 135 since the respective cross sectional areas of pre-filling chamber 125 and ejection chamber 130 are held constant, the cycle time can be shortened by increasing the inflow pressure, thereby increasing the pressure gradient acting on plate 135. Therefore, the VAT) 100 provides a shorter cycle time as the inlet pressure increases. The inflow pressure for device 100 is generally the "left atrial pressure" of the patient This automatically increases when patients that perform some sort of physical activity, where the need for cardiac output increases with the level of physical activity. Since VAD 100 will respond to increased inflow pressure by relocating the movable-plate 135 faster, a higher output per minute results based on the level of the physical activity. Thus, VADs according to the invention are truly self-regulating At higher frequency and resulting increased pumping rates, it is possible that the kinetic energy of the incoming blood might be so high that it results in both the one way valve 140 and the outlet valve 145 to both be opened when movable-plate 135 has come to its lowermost position. If VAD 100 is operated at a relative high frequency (>100 beats per minute) the inflowing blood will be accelerated during pump systole. When movable plate 135 has reached its end position in the cycle the blood in the pre-filling chamber 125 will still strive to move forward due to the kinetic energy/momentum built up in that mass. As a result the blood can continue to flow through the one-way valve 140 for a period of time even after the movable plate 135 has reached its end position. This flow will result in a pressure build up in the ejection chamber 130, which will increase the pressure gradient acting on the movable plate 135, resulting in a quicker relocation of movable plate 135. At ever higher frequencies it is possible that the momentum of the inflowing blood will create a high enough pressure in the ejection chamber 130 so that it exceeds the aortic pressure. This can result in a small addition to VAD outflow, beyond the point of where the movable plate 135 has reached its end position. Thus, blood output by VAD 100 at high frequency might exceed the output that can be calculated from actual VAD stroke volume. An analogous condition is known to occur in the human heart.

If the ejection phase time is equal to the relocation phase time of movable plate 135, the inflow rate will be constant, but the outflow rate will be pulsating. This is because the active filling chamber volume changes during the cycle. As the movable plate 135 moves down the active filling chamber is the pre-filling chamber 125 alone. During about 50% of the VAD cycle time pre-filling chamber 125 goes from a fully compressed state with zero volume to a fully extended state with a volume equal to about one half that of the ejection chamber 130. At the same time, the ejection chamber 130 goes from its extended state to its compressed state, ejecting its stroke volume. During this phase, valve 140 is closed, but the outflow valve 145 is open. When the movable plate 135 starts moving back up the outflow valve 145 closes and valve 140 opens. In this arrangement, the active filling chamber is the pre-filling chamber 125 together with the ejection chamber 130. During this phase of plate 135 relocation the volume of the pre-filling chamber 125 will go from its maximum to zero, but the volume of the ejection chamber 125 will go from its minimum to its maximum. The result is a total volume increase equal to the pre-filling volume (or 50% of the ejection chamber volume). Some important consequences result from the flow dynamics of VAD 100 described above.

The pulsating outflow obtained from VAD 100 is more physiologically correct compared to other constant outflow VAD's. Constant inflow may reduce blood exposure to pump surfaces, thereby minimizing the risk of potentially life threatening thrombosis. Since there will be a kinetic energy (a momentum) in the inflowing blood, the blood will tend to continue to flow even when the movable plate 135 has reached the end position. At high pump frequencies, this will likely result in an additional small volume being ejected from the pump. Thus, the output from VAD 100 will (at high pump frequencies) be greater than the frequency times the stroke volume (ejection chamber volume). It is therefore more efficient than an ordinary displacement pump. Increased efficiency enables fabrication of a pump having a smaller stroke volume.

Moreover, due to the constant inflow feature of VAD 100, filling is not limited to only during a predetermined filling phase. This feature allows for an even smaller pump with comparable output capacity as compared to the currently available displacement pumps. Small size designs have proven to be a crucial feature in bridge-to-transplant and destination therapy VAD systems that ideally are designed as totally implantable systems. VADs according to the invention can be further miniaturized, such as noted above by designing pre-filling chamber 125 to have a near zero or zero volume in its compressed state. A smaller size can also be achieved using the output efficiency increase with frequency provided by VADs according to the invention. Due to the likelihood of an additional small volume addition to output during high frequency operation, VADs according to the invention may purposely be operated at a high frequency. This will allow for a pump embodiment with a smaller stroke volume, while preserving the same output range as before, further minimizing the size of the device. Miniaturization enables VADs according to the invention to be placed in very small volumes, such provided by pediatric patients. This inventive feature is expected to be significant since most current displacement VAD's exclude pediatric patients based solely on size restrictions.

VAD 100 can be designed from largely standard components and be made modular, separating blood contacting surfaces from the powering (actuation) module, if needed. This design would not likely be used for implantable VAD systems according to the invention. However, such a version could be made for shorter term use in settings such as the ER, ICU or PTCA laboratory. In such settings, such a VAD system can be used for instance for cardiogenic shock. The system could then be external to the patient with peripheral cannulae accessing the systemic circulation. The powering module (such as a coil for electromagnetic actuation) would be reusable and a disposable pump housing could be mounted on the powering module (permanent magnet in the movable platform).

Due to the self-regulating feature, VAD 100 will also eliminate the need for complex computerized management and control systems and thus overcome this shortcoming of the available VAD systems. Moreover, VAD 100 will enable ease of use even to less experienced users through its self-regulating mechanism, expanding the field of use to interventional cardiologists and emergency medical specialists for applications such as cardiogenic shock.

The multi-chamber VADs according to the invention will provide improved alternatives for use as a totally implantable bridge-to-transplant or destination therapy VAD system. This approach would involve using VAD systems according to the invention as a left or right VAD, bypassing the human heart. As a left VAD, blood is drawn from the left ventricular chamber or left atrial chamber to the VAD and then back to the ascending or descending aorta will enable taking over parts or all of the hearts pumping, reducing the pressure of the blood going in to the diseased heart (preload). As a right VAD, blood is drawn from the right ventricular chamber or right atrial chamber to the VAD and then back to the pulmonary trunk.

The ease of use of VADs according to the invention along with reduced device and maintenance costs would also make this a highly attractive design for external bridge-to-recovery approaches. The design can facilitate a fast minimally invasive implantation procedure using peripheral artery cannulation. This approach would involve drawing blood from the descending aorta to the VAD and returning blood to descending aorta. This would decrease the systemic blood pressure (afterload), reducing the amount of work required by the diseased heart. This approach is likely to vastly expand the market for such a device, enabling trauma specialists, cardiologists and other non-surgical specialists to use the device in non-surgical settings.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A multi-chamber ventricular assist device (VAD) for pumping blood, comprising:
   a rigid outer housing having an inlet and outlet;
   a pre-filling chamber disposed within said housing fluidly connected to said inlet;
   an ejection chamber disposed within said outer housing;
   a movable plate flexibly secured to said housing in a flow path of said blood, said movable plate disposed between said pre-filling and said ejection chamber, said movable plate having a one way valve for flowing blood from said pre-filling chamber to said ejection chamber;

an outlet valve disposed between said ejection chamber and said outlet, and structure for moving said movable plate.

2. The VAD of claim 1, wherein said pre-filling chamber is a flexible chamber.

3. The VAD of claim 1, wherein said flexible chamber is spaced apart front inner walls of said housing, wherein a gas holding chamber is formed between said flexible chamber and said housing.

4. The VAD of claim 3, wherein a pressure differential between said gas holding chamber and said ejection chamber provides a passive driving force for automatic movement of said movable plate upward toward said pre-filling chamber.

5. The VAD of claim 4, wherein a cross sectional area of said pre-filling and said ejection chamber remains substantially constant throughout cycling of said device.

6. The VAD of claim 5, wherein a blood pumping rate of said VAD monotonically increases with increasing inflow pressure at said inlet, whereby said VAD is self-regulating.

7. The VAD of claim 1, wherein said ejection chamber includes rigid walls.

8. The VAD of claim 7, wherein said rigid walls of said ejection chamber are provided by inner walls of said outer housing.

9. The VAD of claim 7, wherein said rigid walls include a textured surface, said textured surface promoting neointima formation.

10. The VAD of claim 1, wherein a maximum volume of said pre-filling chamber is substantially less than a maximum volume of said ejection chamber.

11. The VAD of claim 10, wherein said maximum volume of said pre-filling chamber is in a ratio with said maximum volume of said ejection chamber of between 1.5:1 and 3:1.

12. The VAD of claim 1, wherein said outer housing is hermetically sealed.

13. The VAD of claim 1, wherein said pump provides a continuous inflow of blood throughout a duration of a complete pumping cycle.

14. The VAD of claim 13, wherein said inflow is a substantially constant inflow rate throughout said pumping cycle.

15. A self-regulating method of pumping blood using a ventricular assist device (VAD) disposed within a cardiac patient, comprising the steps of:

receiving a variable inflow pressure, and automatically providing an output flow rate of blood based on said inflow pressure, wherein a rate of said blood flow monotonically increases with a level of physical activity performed by said patient.

16. The method of claim 15, wherein said inflow pressure is atrial pressure.

17. The method of claim 15, wherein said output flow is a pulsating flow.

18. The method of claim 15, wherein said VAD includes a textured surface in contact with said blood, said textured surface promoting neointima formation.

19. The method of claim 15, wherein a continuous inflow of blood throughout a duration of a complete pumping cycle is provided.

20. The VAD of claim 19, wherein said inflow is a substantially constant inflow rate throughout said pumping cycle.

* * * * *